United States Patent [19]
Signorino

[11] 3,981,984
[45] Sept. 21, 1976

[54] COLOR FILM COATING OF TABLETS AND THE LIKE

[75] Inventor: Charles A. Signorino, King of Prussia, Pa.

[73] Assignee: Colorcon Incorporated, West Point, Pa.

[22] Filed: June 30, 1972

[21] Appl. No.: 268,014

Related U.S. Application Data

[63] Continuation-in-part of Ser. No. 717,984, April 1, 1968, abandoned.

[52] U.S. Cl. .................................. 424/33; 424/34; 424/35; 424/36; 260/33.4 R; 106/154 Z; 106/187; 106/189; 106/190; 106/193 D; 106/193 J; 106/198; 106/308 C; 106/308 P; 106/308 M; 106/308 R

[51] Int. Cl.$^2$ .................. A61K 9/32; A61K 9/34; A61K 9/36; A61K 9/38; C08K 1/14; C08K 1/26

[58] Field of Search .......................... 424/34–38, 424/33; 100/209; 106/154, 189, 190, 193, 198, 308; 260/33.4

[56] References Cited
UNITED STATES PATENTS

| | | | |
|---|---|---|---|
| 2,211,912 | 8/1940 | Ryan | 260/40 |
| 2,304,308 | 12/1942 | Hurd | 106/308 P X |
| 2,441,927 | 5/1948 | Adams | 106/293 |
| 3,079,303 | 2/1963 | Raff | 424/34 |
| 3,449,489 | 6/1969 | Gaunt | 424/31 |
| 3,524,756 | 8/1970 | Signorino et al. | 424/34 X |
| 3,551,133 | 12/1970 | Sprayberry | 424/34 |

Primary Examiner—Theodore Morris
Attorney, Agent, or Firm—Smith, Harding, Earley & Follmer

[57] ABSTRACT

A pigment suspension for a film coating for tablets and the like comprising a solvent, pigment particles dispersed in the solvent, and a low molecular weight alcohol soluble polymer which acts as a protective colloid coating the pigment particles and providing for a higher concentration of pigment particles in the pigment suspension. The method of making the pigment suspension comprises the steps of pouring a solvent into a container, stirring the pigment particles into the solvent to disperse the pigment particles evenly, stirring a protective colloid into the liquid in the container and dispersing it therethrough to make the liquid less viscous and more adaptable for accepting additional pigment particles, and stirring additional pigment particles into the container liquid to obtain the desired pigment suspension.

A coating suspension for tablets and the like comprising the pigment suspension dispersed in a polymer solution. The method of making the coating suspension includes dispersing a powdered polymer in a first liquid solvent, stirring a second solvent into the liquid until all of the polymer is in solution, and stirring the pigment suspension into the polymer solution.

A coated tablet and the like having as the coating material in a thin film comprising a polymer having pigment particles dispersed therethrough, and a protective colloid coating the pigment particles.

32 Claims, No Drawings

COLOR FILM COATING OF TABLETS AND THE LIKE

Cross Reference To Related Patents

This patent application is a continuation-in-part of my patent application Ser. No. 717,984, filed Apr. 1, 1968, now abandoned.

BACKGROUND OF THE INVENTION

The film coating of solid forms such as pharmaceutical tablets, gum and confectionery pieces is increasing rapidly over other methods, such as sugar coating. Film coating has many advantages over other coating techniques, including greater efficiency, better control, and better uniformity and reproducibility of color. Endicott et al., U.S. Pat. No. 2,881,085, issued Apr. 7, 1959, and Endicott et al., U.S. Pat. No. 2,954,323, issued Sept. 27, 1960, disclose thin film coating for tablets and the like.

One of the technical problems existing for some time in the art of film coating is that of producing a color coating which may be reproduced reliably over and over again so that all batches of tablets are colored the same. One of the difficulties arises from the limited solubility of standard food color dyes in the coating solution, which results in an inability to produce fine suspensions of insoluble pigments and causes rough coatings and mottled or uneven color finishes.

Another problem arises from the fact that water is detrimental to the stability of a solid form such as a pharmaceutical tablet. Accordingly, anhydrous organic solvents are desirable as the solvent for the coloring material, but most dyes are insoluble in such solvents.

Another problem is presented by the desire to produce a smooth elegant finish on the tablets, which requires a low concentration of polymer or film-former in the coating suspension, and also a low concentration of pigments in large volumes of volatile solvents. Because of the low concentration of pigments and polymers in the solvents, producing a fine dispersion of the pigment particles in the polymer has been very difficult. In one prior technique (Endicott et al., U.S. Pat. No. 2,954,323, column 6, lines 18–19, for example), the coating suspension was ground in large ball mills for lengthy periods of time, in the order of 8 to 16 hours. This is a very time-consuming and expensive technique.

SUMMARY OF THE INVENTION

It is an object of this invention to provide a pigment suspension and a coating suspension which overcomes the problems of the prior art.

It is another object to provide a pigment and a coating suspension having colors which are reproduced reliably and which are so dispersed in solvents as to produce fine suspensions of insoluble pigments.

It is another object to produce pigment and coating suspensions which use anhydrous organic solvents and thereby enhance the stability of the coated tablets because of the absence of water.

It is another object to make the suspensions by a method which requires only stirring, and eliminates the necessity of using large ball mills for extended periods of time.

These results are accomplished by stirring very fine pigment particles into a solvent to form a suspension, stirring a protective colloid into the suspension to make it less viscous and more adaptable for accepting additional pigment particles, and stirring additional pigment particles into the suspension to obtain the desired pigment suspension. Then the pigment suspension is stirred into a polymer solution to obtain a coating suspension which is adapted to be applied to tablets and the like by using the usual tablet coating techniques, such as pan coating.

DESCRIPTION OF THE PREFERRED EMBODIMENT

In accordance with the invention, the method of making a pigment suspension for a film coating for tablets and the like comprises the steps of pouring solvent into a container, stirring pigment particles into the solvent to disperse the pigment particles evenly, stirring a protective colloid into the liquid in the container and dissolving it therethrough to make the liquid less viscous and more adaptable for accepting additional pigment particles, and stirring additional pigment particles into the container liquid to obtain the desired pigment suspension.

The most desirable solvents for the pigment suspension are ethanol and isopropyl alcohol because a pigment suspension made with these solvents is dispersible in all polymer solutions to make a coating suspension. However, the pigment suspension may be produced using the following solvents: methanol, ethanol, isopropanol, acetone, mixtures of the solvents, or mixtures of the solvents with chlorinated hydrocarbons.

The pigment suspension may be used to color any of the currently used film coating polymer solutions including solutions of shellac, zein, PVP (polyvinyl pyrrolidone), CAP (cellulose acetate phthalate), PVAP (polyvinyl acetate phthalate), Methocel, Ethocel, Eudragit, Carbowax, and other synthetic resins and film-formers. An illustrative list of film formers is given in Gaunt U.S. Pat. No. 3,449,489, which issued June 10, 1969 on an application filed Oct. 21, 1965.

Methocel is hydroxypropyl methyl cellulose sold by Dow Chemical Co., Ethocel is Dow Chemical's brand of ethyl cellulose, and Carbowax is polyethylene glycol sold by Union Carbide Co.

Methocel is presently the most popular film former for film coating pharmaceutical tablets. Eudragit, though not very popular in the United States, is a useful acrylic resin sold by Rohm & Haas, Germany.

The pigment concentrate is made by dispersing the pigment particles in the solvent in an apparatus that uses a very high mechanical work input. One such piece of equipment is the Kady mill, which operates on a kinetic principle and is manufactured by the Kinetic Dispersion Equipment Company. In a Kady mill, the pigment particles are dispersed in the solvent by being rotated in such a manner as to impinge upon a static blade at a very high speed. The material in the mill must be kept very fluid.

The pigment concentrate is made by adding the pigment particles to the solvent. As the quantity of pigment particles increases, the viscosity of the mixture increases and when it starts to get too viscous, a low molecular weight alcohol soluble polymer, such as hydroxypropyl cellulose, is added to the mixture as a protective colloid or dispersing agent. The viscosity is immediately reduced so that more pigment particles may be added. The mill is run at about 5,500 rpm until a good dispersion of the pigment particles in the solvent is achieved.

Pigments which may be used to make the pigment suspension include: titanium dioxide, magnesium carbonate, talc, silica gel, iron oxides, channel black, FD&C and D&C Lakes and insoluble dyes. Suitable pigments are also listed in Jeffries U.S. Pat. No. 3,149,040, and Butler et al. U.S. Pat. No. 3,297,535. Additionally, quantities of dyes soluble in the solvent may be added as an adjunct to the pigments without difficulty. Excellent dispersions are achieved, especially if finely ground pigment particles are used. This dispersion technique is excellent for breaking up agglomerates and for dispersing the individual pigment particles for good suspension in the solvent. The pigment particles remain in suspension, with very few settling problems.

The concentration of the pigment solid in the pigment suspension is determined by the bulking density of the pigments used. Titanium dioxide and iron oxide are suspended to 50 - 60% by weight. The lakes are suspended to about 35% by weight. Channel black is suspended to about 25%. A mixture of equal parts of titanium dioxide and lakes is suspended to about 45% pigments by weight. The quantity of hydroxypropyl cellulose solids may be about 0.5 to 10%, and most preferably about 2 - 3% by weight of the pigment suspended. Excellent results were obtained where the hydroxypropyl cellulose solids were in the range of about .5 to 5% by weight of the pigment suspended, with a preferred range being about 1 to 3%.

Instead of hydroxypropyl cellulose, other low molecular weight alcohol soluble polymers having a molecular weight in the range of about 20,000 to 160,000, may be used as protective colloids, including polyvinylpyrrolidone, ethyl cellulose, and polyethylene glycol. *Hackh's Chemical Dictionary*, Third Edition, page 213, defines "protective colloid" as a substance which promotes the stability of a heterogeneous system, or of the colloidal state, by enveloping particles. The term protective colloid is well known in the art and is used, for example, in Lee U.S. Pat. No. 3,413,400 which issued Nov. 26, 1968, on an application filed Aug. 27, 1964, and is used in a 1964 publication of General Aniline & Film Corporation entitled *PVP* (polyvinylpyrrolidone) (see especially page 12).

Hydroxypropyl cellulose is sold by Hercules, Inc. under its trademark Klucel, ethyl cellulose is sold by Dow Chemical under its trademark Ethocel, and polyethylene glycol is sold by Union Carbide under its trademark Carbowax.

Any of the commonly used film formers and film forming polymers may be used as a protective colloid so long as they are soluble in alcohol, and may also be used in the polymer solution, except those which are not soluble in alcohol compatible solvents.

The following examples illustrate the invention.

EXAMPLE 1

A pigment suspension is made up according to the following formula:

| | |
|---|---|
| 90 oz. | 3A Alcohol |
| 10 oz. | D&C Red No. 7 Lake |
| 31 oz. | FD&C Yellow No. 5 Lake |
| 12 oz. | Titanium Dioxide |
| 4½ oz. | Talc |
| 1½ oz. | Hydroxypropyl cellulose (Klucel) |

The alcohol is poured into a 1 gallon Kady mill, and one half of the powdered lakes, titanium dioxide and talc are stirred into the solvent, and the Kady mill is turned on for a few seconds to disperse the pigment particles in the solvent. Then the hydroxypropyl cellulose is added and is dispersed in the solvent for a few seconds. Then the remainder of the pigment particles are stirred into the mix, and the Kady mill is turned on for 4 minutes to disperse the solids in the solvent. The resulting red suspension is 40% solids and is quite fluid. The hydroxypropyl cellulose is about 2.68% by weight of the pigment particles. The suspension is quite stable and resists settling.

Example 1a

A pigment suspension is made in accordance with Example 1 except that 1½ oz. of PVP (polyvinylpyrrolidone) is substituted for the 1½ oz. of hydroxypropyl cellulose.

Example 1b

A pigment suspension is made in accordance with Example 1 except that 1½ oz. of Ethocel (hydroxypropyl ethyl cellulose) is substituted for the 1½ oz. of hydroxypropyl cellulose.

Example 1c

A pigment suspension is made in accordance with Example 1 except that 1½ oz. of Carbowax (Union Carbide's polyethylene glycol) is substituted for the 1½ oz. of hydroxypropyl cellulose.

EXAMPLE 2

A pigment suspension is made up according to the following formula:

| | |
|---|---|
| 81 oz. | 3A Alcohol |
| 7 oz. | FD&C Blue No. 1 Lake |
| 22 oz. | FD&C Yellow No. 5 Lake |
| 22 oz. | Titanium Dioxide |
| 1 oz. | Hydroxypropyl Cellulose |

The ingredients are mixed in accordance with the method of Example 1 to produce a green suspension containing 39% solids. The hydroxypropyl cellulose is about 1.92% by weight of the pigment particles.

Example 2a

A pigment suspension is made in accordance with Example 2 except that 1 oz. of hydroxypropyl cellulose is used, and is about 0.96% by weight of the pigment particles.

Example 2b

A pigment suspension is made in accordance with Example 2 except that 2½ oz. of hydroxypropyl cellulose is used, and is about 4.8% by weight of the pigment particles.

Example 2c

A pigment suspension is made in accordance with Example 2 except that 1½ oz. of hydroxypropyl cellulose is used, and is about 1.98% by weight of the pigment particles.

Example 2d

A pigment suspension is made in accordance with Example 2 except that 10 oz. of hydroxypropyl cellulose is used, and is about 9.6% by weight of the pigment particles.

EXAMPLE 3

A pigment suspension is made up according to the following formula:

| | |
|---|---|
| 108 oz. | 3A Alcohol |
| 9 oz. | FD&C Red No. 3 Lake |
| 40 oz. | FD&C Yellow No. 5 Lake |
| .37 oz. | Channel Black |
| 26 oz. | Titanium Dioxide |
| 2 oz. | Hydroxypropyl Cellulose |

The ingredients are mixed in accordance with the procedure of Example 1 to produce a brown suspension containing 42% solids. The hydroxypropyl cellulose is about 1.75% by weight of the pigment particles.

EXAMPLE 4

A pigment suspension is made up according to the following formula:

| | |
|---|---|
| 432 oz. | 3A Alcohol |
| 11¼ oz. | Low Opacity Yellow Oxide |
| 1½ oz. | Red Oxide |
| .56 oz. | Black Oxide |
| 324 oz. | Titanium Dioxide |
| 27 oz. | Talc |
| 9 oz. | Hydroxypropyl Cellulose |

The ingredients are mixed in accordance with the method of Example 1 to produce a light yellow suspension containing 47% solids. The hydroxypropyl cellulose is about 2.1% by weight of the pigment particles.

EXAMPLE 5

A pigment suspension is made up according to the following formula:

| | |
|---|---|
| 108 oz. | 3A Alcohol |
| 24 oz. | FD&C Yellow No. 5 Lake |
| 12 oz. | FD&C Yellow No. 6 Lake |
| 30 oz. | Titanium Dioxide |
| 1.6 oz. | Hydroxypropyl Cellulose |

The ingredients are mixed in accordance with the method of Example 1 to produce a yellow suspension containing 42% solids. The hydroxypropyl cellulose is about 2.36% by weight of the pigment particles.

Example 5a

A pigment suspension is made up according to the following formula:

| | |
|---|---|
| 296 oz. | SDA 3-A Alcohol |
| 100 oz. | Titanium Dioxide |
| 100 oz. | FD&C Green No. 3 Lake |
| 2 oz. | Hydroxypropyl Cellulose (Klucel L.F.) ("L.F." is Hercules' symbol for 75,000 molecular weight, food grade) |

The ingredients are mixed in accordance with the method of Example 1 to produce a pigment suspension containing 42.3% solids. The hydroxypropyl cellulose is about 1% by weight of the pigment particles.

Example 5b

A pigment suspension is made up according to the following formula:

| | |
|---|---|
| 276 oz. | SDA 3-A Alcohol |
| 100 oz. | Titanium Dioxide |
| 100 oz. | FD&C No. 6 Lake |
| 3 oz. | Polyvinylpyrrolidone K-30 ("K-30" is GAF Corp.'s designation for polyvinylpyrrolidone molecular weight 40,000) |

The ingredients are mixed in accordance with the method of Example 1 to produce a pigment suspension containing 42.4% solids. The PVP is about 1½% by weight of the pigment particles.

Example 5c

A pigment suspension is made up according to the following formula:

| | |
|---|---|
| 276 oz. | SDA 3-A Alcohol |
| 100 oz. | Titanium Dioxide |
| 50 oz. | FD&C Yellow No. 5 Lake |
| 50 oz. | FD&C Violet No. 1 Lake |
| 4 oz. | Polyethelene Glycol (Carbowax 4,000, Union Carbide's 160,000 molecular weight polyethelene glycol) |

The ingredients are mixed in accordance with the method of Example 1 to produce a pigment suspension containing 42.5% solids. The polyethelene glycol is 2% by weight of the pigment particles.

Example 5d

A pigment suspension is made up according to the following formula:

| | |
|---|---|
| 300 oz. | SDA 3-A Alcohol |
| 100 oz. | Titanium Dioxide |
| 50 oz. | FD&C Blue No. 2 Lake |
| 50 oz. | FD&C Red No. 3 Lake |
| 4 oz. | Ethyl Cellulose (Dow Chemical's Ethocel 10 cps) |

The ingredients are mixed in accordance with the method of Example 1 to produce a pigment suspension containing 40.5% solids. The ethyl cellulose is about 2% by weight of the pigment particles.

The following examples will illustrate the making up of a color coating suspension from a pigment suspension dispersed in a polymer solution.

EXAMPLE 6

To color a solution of Methocel (Dow Chemical's hydroxypropyl methyl cellulose, a film coating polymer), disperse 40 grams of powdered Methocel in 300 grams of methanol (a first solvent which disperses the polymer), than add slowly with stirring 700 grams of methylene chloride, a chlorinated hydrocarbon which serves as a liquid solvent (a second solvent which solubilizes the polymer). Stir until all of the polymer is in solution. To this polymer solution, add 40 ml of the pigment suspension from Example 1. The pigment suspension stirs in with ease. A spatula is used to stir the suspension into the polymer solution. The pigment particles are distributed easily and a good coating suspension results.

Example 6a

The polymer solution of Example 6 may be a plasticized solution. For example, 8 grams of Carbowax 400 (Union Carbide's 16,000 molecular weight polyethylene glycol) is mixed into the polymer solution of Example 6 to plasticize the Methocel.

EXAMPLE 7

A polymer solution is made up according to the following formula:

| | |
|---|---|
| 150 g | Cellulose Acetate Phthalate |
| 350 ml | Acetone |
| 37.5 g | Diethyl Phthalate |
| 1,000 mlqs | Methylene Chloride |

The acetone is placed in a container and the cellulose acetate phthalate is added with stirring to get a polymer solution. After the polymer is completely dissolved, the diethyl phthalate is added as well as a quantity sufficient of methylene chloride to bring the mixture up to 1 liter. The diethyl phthalate plasticizes the cellulose acetate phthalate. The acetone and methylene chloride are preferred solvents for cellulose acetate phthalate because the methylene chloride reduces the explosive hazard of the acetone vapor evaporating. Then 50 ml of the pigment suspension of Example 4 is slowly added to the polymer solution by stirring with a statula to obtain a coating suspension.

The pigment suspension of this invention, made and sold by Colorcon, Inc., West Point, Pennsylvania, under the trademark OPASPRAY, is compatible with film forming solutions whether they be plasticized or not. In general, any non-toxic, food grade plasticizing agent, or mixtures thereof, may be used which is soluble in the solvent used in preparing the film forming solution. Plasticizing agents found to be useful in film-forming solutions include propylene glycol, glycerin, diesters of phthalic acid, i.e., diethyl phthalate, acetylated monoglycerides, triacetin, and polyethylene glycol 400 (Carbowax 400, Union Carbide's 16,000 molecular weight polyethylene glycol).

The pigment suspensions of the present invention are compatible with all the polymer solutions now being used in film coating. Any of the pigment suspensions of this invention may be used with the polymer solutions of Examples 6, 6a and 7.

The term "3A Alcohol" as used in this specification, is defined as being industrial SDA (Specially Denatured Alcohol) containing 100 gallons of grain alcohol to 5 gallons of methanol.

It is very difficult to disperse solid pigment particles into a polymer or film-forming solution. But it is very easy to disperse my pigment suspension into a polymer or film-forming solution by simple stirring. Accordingly, it is very important that my pigment suspension be in free-flowing liquid form, not a cake or slurry.

It is an object of this invention to provide a pigment suspension which has a very high pigment particle content so that it may be transported to a customer in small containers, and may be dispersed by the customer easily into a film-forming polymer solution by simple stirring, with the pigment particle concentration in the pigment suspension being very high so that it may be dispersed into a large volume of film-forming polymer solution.

I claim as my invention:

1. A high-concentration pigment suspension for a polymer film coating of tablets and the like comprising a non-aqueous solvent, pigment particles dispersed in the solvent, and an edible protective colloid coating the pigment particles, said colloid being about 2.5% by weight of the pigment particles, and the percentage of solids in the suspension being about 39–47%.

2. The pigment suspension of claim 1 wherein the solvent is 3A alcohol.

3. The pigment suspension of claim 1 wherein the pigment particles are D&C and FD&C Lakes.

4. The pigment suspension of claim 1 wherein the colloid is hydroxypropyl cellulose.

5. The pigment suspension of claim 1 wherein the ingredients consist essentially of, in parts by weight, the solvent is 90 parts of 3A alcohol, the pigment particles are 10 parts D&C Red No. 7 Lake, 31 parts FD&C Yellow No. 5 Lake, 12 parts titanium dioxide, 4½ parts talc, and the protective colloid is 1½ parts hydroxypropyl cellulose.

6. The pigment suspension of claim 1 dispersed in an edible solution to form a coating suspension adapted for use as a film coating for tablets and the like.

7. The coating suspension of claim 6 wherein the polymer solution is, in parts by weight, 40 methocel dissolved in 300 methanol and 700 methylene chloride.

8. The coating suspension of claim 6 wherein the polymer solution is 150 grams of cellulose acetate phthalate plasticized by 37.5 grams of diethyl phthalate and dissolved in 350 ml of acetone and a quantity sufficient of methylene chloride to make 1,000 ml of polymer solution.

9. The pigment suspension of claim 1 dispersed in an edible polymer solution to form a coating suspension adapted for use as a film coating for tablets and the like, said polymer being methocel, cellulose acetate phthalate, shellac or zein.

10. A method of making a high-concentration pigment suspension for a film coating for tablets and the like comprising pouring a non-aqueous solvent into a container, stirring pigment particles into the solvent to disperse the pigment particles evenly, reducing the viscosity of the resulting mixture by stirring an edible protective colloid into the liquid in the container and dispersing it therethrough to coat the pigment particles with said protective colloid thereby making the resulting pigment suspension more adaptable for accepting additional pigment particles, and stirring additional pigment particles into the container liquid and coating said additional pigment particles with said colloid to obtain the desired high-concentration pigment suspension, said colloid being about 2.5% by weight of the pigment particles, and the percentage of solids in the suspension being about 39–47%.

11. The method of claim 10 wherein the container is a high speed mill, and the stirring is done by operating the mill at about 5,500 rpm.

12. The method of claim 10 wherein the container is a high speed mill, and by weight the ingredients consist essentially of, the solvent is 81 parts 3A alcohol, the pigment particles are 7 parts FD&C Blue No. 1 Lake, 38 parts FD&C Yellow No. 5 Lake, 38 parts titanium dioxide, and the colloid is 1 part hydroxypropyl cellulose, the alcohol is poured into the mill, half the pigment particles are stirred at high speed into the alcohol for a few seconds, the hydroxypropyl cellulose is stirred at high speed into the liquid for a few seconds, then the other half of the pigment particles are stirred into the liquid at high speed for about 4 minutes, whereby to obtain the desired pigment suspension.

13. The method of claim 10 including dispersing a powdered polymer in a first liquid solvent, stirring a second solvent into the liquid until all the polymer is in solution, and stirring said pigment suspension into the polymer solution to obtain a coating suspension adapted for use as a film coating for tablets and the like.

14. The method of claim 13 wherein the powdered polymer is 40 grams of methocel, the first liquid solvent is 300 grams of methanol, the second solvent is 700 grams of methylene chloride, and 40 ml of said pigment suspension is stirred into the polymer solution, said pigment suspension including, in parts by weight, 90 parts of 3A alcohol, the pigment particles are 10 parts D&C Red No. 7 Lake, 31 parts FD&C Yellow No. 5 Lake, 12 parts titanium dioxide, 4½ parts talc, and the protective colloid is 1½ parts hydroxypropyl cellulose.

15. The method of claim 13 wherein the powdered polymer is 150 grams of cellulose acetate phthalate, the first liquid solvent is 350 ml of acetone, a plasticizer is stirred into the solution of cellulose acetate phthalate and acetone, the second solvent is quantity sufficient of methylene chloride to make 1,000 ml of polymer solution, and 50 ml of said pigment suspension is stirred into the polymer solution, said pigment suspension including, in parts by weight, 432 3A alcohol, 11¼ low opacity yellow oxide, 1½ red oxide, 0.56 black oxide, 324 titanium dioxide, 27 talc, and 9 hydroxypropyl cellulose.

16. The method of claim 10 including dispersing an edible powdered polymer in a first liquid solvent, stirring a second solvent into the liquid until all the polymer is in solution, and stirring said pigment suspension into the polymer solution to obtain a coating suspension adapted for use as a film coating for tablets and the like, said polymer being selected from the group of methocel, cellulose acetate phthalate, shellac, and zein.

17. A coated tablet and the like having as the coating material a thin film comprising an edible polymer having pigment particles dispersed therethrough, and an edible protective colloid enveloping the pigment particles, said colloid being about 2.5% by weight of the pigment particles.

18. The coated tablet of claim 17 wherein the pigment particles are D&C and FD&C Lakes.

19. The coated tablet of claim 17 wherein the colloid is hydroxypropyl cellulose.

20. The coated tablet of claim 17 wherein the ingredients consist essentially of the polymer is methocel, the pigment particles are D&C Red No. 7 Lake, FD&C Yellow No. 5 Lake, titanium dioxide, and talc, and the protective colloid is hydroxypropyl cellulose.

21. The coated tablet of claim 17 wherein the ingredients consist essentially of the polymer is cellulose acetate phthalate which is plasticized by diethyl phthalate, the pigment particles are low opacity yellow oxide, red oxide, black oxide, titanium dioxide, and talc, and the protective colloid is hydroxypropyl cellulose.

22. A high-concentration pigment suspension for dispersing into a film-forming solution to form a coating suspension for film coating pharmaceutical tablets and the like, comprising a non-aqueous solvent, pigment particles dispersed in the solvent, and hydroxypropyl cellulose enveloping the pigment particles, said hydroxypropyl cellulose being about 1 to 5% by weight of the pigment particles, and the percentage of solids in the suspension being about 39–47%.

23. The pigment suspension of claim 22, said hydroxypropyl cellulose being about 2–3% by weight of the pigment particles.

24. A high-concentration pigment suspension for a polymer film coating of tablets and the like comprising a non-aqueous solvent, pigment particles dispersed in the solvent, and an edible protective colloid enveloping the pigment particles, said colloid being about 1–5% by weight of the pigment particles, and the percentage of solids in the suspension being about 39–47%.

25. A high-concentration edible free-flowing liquid pigment suspension for dispersing into a film-forming solution to color it and form a colored coating suspension for film coating pharmaceutical tablets and the like, consisting essentially of a non-aqueous alcohol solvent, pigment particles dispersed in the solvent, and an alcohol soluble film-former enveloping the pigment particles, said film-former being selected from the group of hydroxypropyl cellulose, polyvinylpyrrolidone, ethyl cellulose, and polyethylene glycol.

26. A high-concentration edible pigment suspension for a polymer film coating of tablets and the like consisting essentially of an alcohol solvent, pigment particles dispersed in the solvent, and hydroxypropyl cellulose, polyvinylpyrrolidone, ethylcellulose, or polyethylene glycol dissolved in said solvent and enveloping the pigment particles and being about 2.5% by weight of the pigment particles, and the percentage of solids in the suspension being about 39–47%.

27. A method of making a high-concentration edible pigment suspension for a film coating system for tablets and the like comprising pouring an alcohol solvent into a container, dispersing edible pigment particles into the solvent uniformly, reducing the viscosity of the resulting mixture by stirring hydroxypropyl cellulose, polyvinylpyrrolidone, ethyl cellulose, or polyethylene glycol into the container and dispersing it through the mixture to envelop the pigment particles thereby making the resulting pigment suspension more fluid and adaptable for accepting additional pigment particles, and dispersing additional edible pigment particles into the suspension, said additional pigment particles being enveloped by said hydroxypropyl cellulose, polyvinylpyrrolidone, ethyl cellulose, or polyethylene glycol to obtain the desired high-concentration pigment suspension, said hydroxypropyl cellulose, polyvinylpyrrolidone, ethyl cellulose, or polyethylene glycol being about 2.5% by weight of the pigment particles, and the percentage of solids in the suspension being about 39–47%.

28. An edible coated tablet and the like having as the coating material a thin film consisting essentially of methocel, cellulose acetate phthalate, shellace, or zein having edible pigment particles dispersed therethrough, and hydroxypropyl cellulose, polyvinylpyrrolidone, ethyl cellulose, or polyethylene glycol enveloping the pigment particles, said hydroxypropyl cellulose, polyvinylpyrrolidone, ethyl cellulose, or polyethylene glycol being about 2.5% by weight of the pigment particles.

29. A high concentration pigment suspension for a polymer film coating of tablets and the like consisting essentially of a non-aqueous solvent, pigment particles dispersed in the solvent, and a protective colloid coating the pigment particles, said colloid being about 2.5% by weight of the pigment particles, and the percentage of solids in the suspension being about 39–47%.

30. The pigment suspension of claim 29 wherein the solvent is 3A alcohol, the pigment particles are D&C and FD&C lakes, and the colloid is hydroxypropyl cellulose.

31. A high-concentration pigment suspension for use in the film coating of tablets and the like comprising a non-aqueous solvent, pigment particles dispersed in the solvent, and an effective amount of a film-former enveloping the pigment particles to produce a high concentration of solids in the suspension in the range of about 39–47%.

32. A high-concentration pigment suspension for film coating of tablets and the like comprising a non-aqueous solvent, pigment particles dispersed in the solvent, and an effective amount of a film-former enveloping the pigment particles, said film-former being about 1 to 5% by weight of the pigment particles to produce a high concentration of solids in the suspension.

* * * * *